(12) United States Patent
Chen et al.

(10) Patent No.: US 10,442,838 B2
(45) Date of Patent: Oct. 15, 2019

(54) LINACLOTIDE SYNTHESIS METHOD

(71) Applicant: HYBIO PHARMACEUTICAL CO., LTD., Shenzhen, Guangdong (CN)

(72) Inventors: Xueming Chen, Guangdong (CN); Jingkang Wu, Guangdong (CN); Pengcheng Mi, Guangdong (CN); Anjin Tao, Guangdong (CN); Jiancheng Yuan, Guangdong (CN)

(73) Assignee: HYBIO PHARMACEUTICAL CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 16/062,079

(22) PCT Filed: Dec. 15, 2016

(86) PCT No.: PCT/CN2016/110106
§ 371 (c)(1),
(2) Date: Jun. 13, 2018

(87) PCT Pub. No.: WO2017/101810
PCT Pub. Date: Jun. 22, 2017

(65) Prior Publication Data
US 2018/0371022 A1  Dec. 27, 2018

(30) Foreign Application Priority Data
Dec. 18, 2015 (CN) .......................... 2015 1 0964573

(51) Int. Cl.
| | |
|---|---|
| *A61K 38/12* | (2006.01) |
| *C07K 7/64* | (2006.01) |
| *C07K 1/04* | (2006.01) |
| *C07K 1/06* | (2006.01) |
| *C07K 1/20* | (2006.01) |
| *C07K 7/08* | (2006.01) |
| *C07K 1/16* | (2006.01) |
| *C12P 21/02* | (2006.01) |

(52) U.S. Cl.
CPC ............... *C07K 7/64* (2013.01); *C07K 1/04* (2013.01); *C07K 1/042* (2013.01); *C07K 1/06* (2013.01); *C07K 1/16* (2013.01); *C07K 1/20* (2013.01); *C07K 7/08* (2013.01); *C12P 21/02* (2013.01); *C12Y 111/01007* (2013.01); *Y02P 20/55* (2015.11)

(58) Field of Classification Search
None
See application file for complete search history.

(56) References Cited

FOREIGN PATENT DOCUMENTS

| | | |
|---|---|---|
| CN | 102875655 A | 1/2013 |
| CN | 103626849 | * 11/2013 |
| CN | 103626849 A | 3/2014 |
| CN | 104163853 A | 11/2014 |
| CN | 104231051 A | 12/2014 |
| CN | 104844693 A | 8/2015 |
| CN | 104974229 A | 10/2015 |
| CN | 105017387 A | 11/2015 |
| WO | 2015/022575 A2 | 2/2015 |

OTHER PUBLICATIONS

Gongora-Benitez, Biopolymers, (Pept Sci) 96: 69-80, 2011 (Year: 2011).*
International Search Report for PCT/CN2016/110106 dated Feb. 24, 2017, ISA/CN.
Miriam Gongora-Benitez et al., "Optimized Fmoc Solid-Phase Synthesis of the Cysteine-Rich Peptide Linaclotide", Biopolymers, vol. 96, No. 1, Jan. 1, 2011 (Jan. 1, 2011), pp. 69-80, XP55047758.
Tobias M. Postma et al., "Disulfide Formation Strategies in Peptide Synthesis", European Journal of Organic Chemistry, vol. 2014, No. 17, Jun. 28, 2014 (Jun. 28, 2014), pp. 3519-3530, XP55174974.
Search Report dated Jul. 11, 2019 for European patent application No. 16874867.1, 6 pages.

* cited by examiner

*Primary Examiner* — Satyanarayana R Gudibande
(74) *Attorney, Agent, or Firm* — Yue (Robert) Xu; Apex Attorneys at Law, LLP

(57) ABSTRACT

Disclosed is a method of synthesizing linaclotide through completely selective formation of three disulfide bonds, comprising the steps of: 1) synthesizing linaclotide precursor resin through solid-phase synthesis; 2) forming the first disulfide bond through solid phase oxidation; 3) forming the second disulfide bond through liquid phase oxidation; and 4) deprotecting methyl in the methyl-protected cysteine, and oxidatively coupling the third disulfide bond to obtain linaclotide. The method has mild reaction conditions with low cost, high yield and high purity product, is a simple and stable process and is suitable for large-scale production.

15 Claims, 1 Drawing Sheet
Specification includes a Sequence Listing.

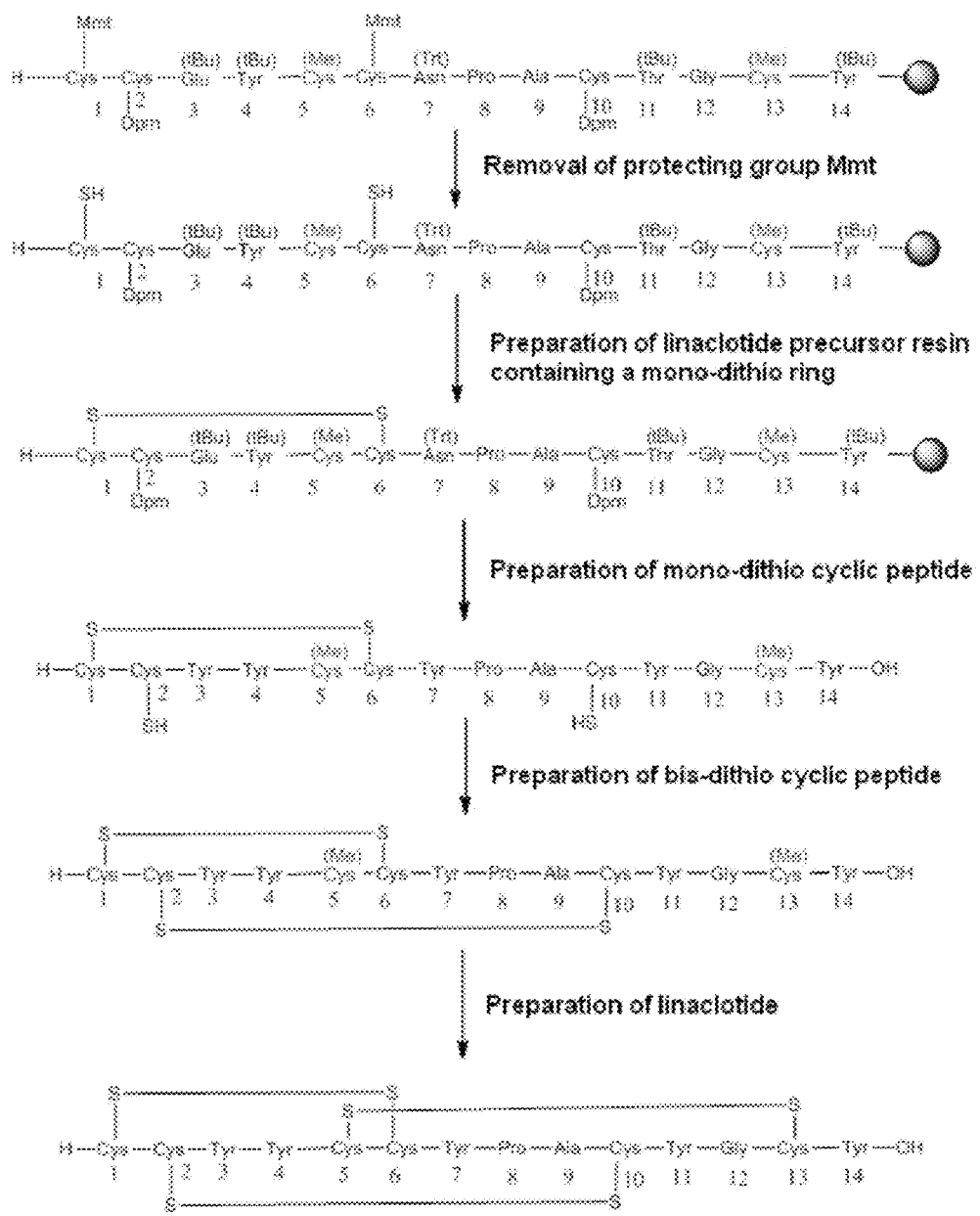

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: Linaclotide

<400> SEQUENCE: 1
```

-continued

```
Cys Cys Glu Tyr Cys Cys Asn Pro Ala Cys Thr Gly Cys Tyr
1               5                   10
```

LINACLOTIDE SYNTHESIS METHOD

This is a US National Phase application based upon PCT Application No. PCT/CN2016/110106, filed Dec. 15, 2016, which claims priority to Chinese Patent Application No. 201510964573.0, filed Dec. 18, 2015, the disclosures of which are hereby incorporated by reference in their entirety.

FIELD

The present invention relates to the technical field of pharmaceutical synthesis, and in particular to a synthesis method of linaclotide.

BACKGROUND

Linaclotide is a GC-C (enterocyte uridylate cyclase C) receptor agonist and was approved by US FDA in August 2012 for the treatment of adult chronic idiopathic constipation and constipation-predominant irritable bowel syndrome (IBS-C). Linaclotide, which is developed by Ironwood Pharmaceuticals, is a polypeptide consisting of 14 amino acids and containing three disulfide bonds in chemical structure thereof, and can be prepared by cell expression and chemical synthesis. Linaclotide has a sequence of Cys-Cys-Glu-Tyr-Cys-Cys-Asn-Pro-Ala-Cys-Thr-Gly-Cys-Tyr (SEQ ID NO: 1) and a structure of:

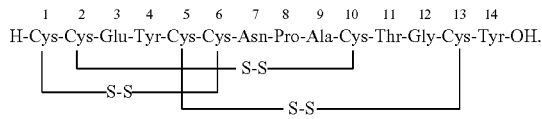

SEQ ID NO: 1 is being submitted as an ASCII text file via EFS-Web, file name Sequence-1, size 461 bytes, created on Jun. 13, 2018, the content of which is incorporated herein by reference.

Benitez et al. published a relevant report on Peptide Science in 2010. Three methods are adopted in the report to try to synthesize linaclotide. In method (1), Trt is used to protect the side chain of Cys, and the linear peptide is synthesized using an Fmoc solid phase peptide synthesis process to obtain a crude peptide, which then is oxidized by one-step using a liquid-phase oxidation process to obtain the target peptide. In method (2), Trt and Acm are used to protect the side chain of Cys, and a partially protected linear peptide is obtained by an Fmoc solid phase peptide synthesis process, and then the synthesis of disulfide bonds is completed using a semi-selective strategy. In method (3), three completely selective strategies are used to synthesize linaclotide, respectively: [2 Mmt+2 Acm+2 Trt], [2 Acm+2 Trt+2 pMeOBzl] and [2 StBu+2 Trt+2 pMeOBzl].

In method (1), the synthesis steps are simple, and only one kind of protecting group for Cys is used. However, for peptides where three disulfide bonds need to be formed site-specifically, many different disulfide-bond mismatched isomers will be obtained by random oxidation. Although it is possible to make the conversion into target molecules in the oxidation process as high as possible by some buffer solution systems, the production of other isomers cannot always be avoided. Such a procedure easily results in a crude target peptide with a lower purity and yield, making it very difficult to achieve large-scale production. Meanwhile, oxidation by this method has a very high dependence on external conditions such as temperature, etc. Under different circumstances, the product yield obtained by natural oxidation also varies greatly, which is not conducive to the control of product quality. Method (2) is a method for semi-selective site-specific oxidation, in which one disulfide bond is site-specifically oxidized, decreasing the number of different isomers formed, as compared with method (1). However, the production of isomers still cannot be avoided. Meanwhile, it is further mentioned directly in the report that two disulfide bonds are formed using iodine oxidation, and the yield of crude peptides is severely reduced. In method (3), the researchers chose to use three different complete selectivity methods to form three disulfide bonds, but no target product is obtained.

At present, there is still no method for preparing linaclotide with a high efficiency. Chinese patents CN 104231051A, CN 104628826A, CN 104163853A, CN 104844693A, and CN 102875655A introduce a method for forming three disulfide bonds by one-step oxidation, wherein a linaclotide resin is firstly synthesized, and then cleaved to remove all protecting groups and resin solid phase carrier to obtain a linaclotide linear crude peptide, which is finally subjected to a one-step oxidation reaction using an oxidation system. Among them, a GHS/GSSH oxidation system is used in CN 104231051A, CN 104163853A, and CN 102875655A; elemental iodine is used to oxidize in a sodium phosphate buffer solution of pH=6~13 in CN 104628826A; and a cysteine hydrochloride/DMSO buffer solution oxidation system is used in CN 104844693A. Although the one-step oxidation method can convert the linear peptide into the target structure as much as possible by the buffer system, the disulfide bond mismatched isomer impurities still cannot be avoided to produce and the yield is lower.

Therefore, it is necessary to explore a linaclotide synthesis method which is performed under mild conditions, low in cost, high in yield, high in product purity, simple and stable in processes, and suitable for large-scale production.

SUMMARY

With respect to the problem existing in the above synthesis methods that isomer impurities are produced due to the disulfide bond mismatch thereby leading to a lower purity and yield of products, the present invention provides a method for synthesizing linaclotide by forming three disulfide bonds with complete selectivity, thereby enabling the efficient site-specific synthesis of three completely intercrossed disulfide bonds.

The raw materials used in the method of the present invention are less costly, and especially a cheaper methyl-protected cysteine is used in the formation of the third disulfide bond. Furthermore, the demethylation and the formation of the third disulfide bond occur in one step simultaneously, which is easy to handle, less costly, and of economic and practical value.

To achieve the above objects, the present invention provides the following technical solutions:

A method for preparing linaclotide, comprising the following steps:

1) preparing a linaclotide precursor resin by reacting Fmoc-Tyr(tBu)-OH with a carrier resin to obtain Fmoc-Tyr(tBu)-resin, and coupling Fmoc-AA-OH one by one in the order from C-terminus to N-terminus with the Fmoc-Tyr(tBu)-resin as a solid phase carrier to obtain the linaclotide precursor resin, wherein the side chains of Cys corresponding to positions 5 and 13 of linaclotide are protected by Me, the side chains of Cys corresponding to positions 1 and 6 of linaclotide are protected by Mmt, and the side chains of Cys corresponding to positions 2 and 10 of linaclotide are protected by Dpm;

2) removing the Mmt protecting groups from the linaclotide precursor resin obtained in step 1) with a deprotecting agent;

3) oxidizing the linaclotide precursor resin obtained in step 2) with an oxidizing agent to form a first disulfide bond to obtain a linaclotide precursor resin containing a mono-dithio ring;

4) cleaving the resin in the linaclotide precursor resin containing a mono-dithio ring obtained in step 3) and simultaneously removing the Dpm protecting groups with a lysing solution to obtain a mono-dithio cyclic peptide;

5) oxidizing the mono-dithio cyclic peptide obtained in step 4) with an oxidizing agent to form a second disulfide bond to obtain a bis-dithio cyclic peptide; and 6) removing the methyl protecting groups of Cys from the bis-dithio cyclic peptide obtained in step 5) and simultaneously oxidizing to form a third disulfide bond to obtain the linaclotide.

In the method for preparing linaclotide of the present invention, the carrier resin in step 1) is wang resin or 2-chloro resin, with a degree of substitution of 0.1-1.0 mmol/g, preferably 0.2-0.8 mmol/g, and more preferably 0.2-0.5 mmol/g.

In the method for preparing linaclotide of the present invention, the coupling of Fmoc-AA-OH in the order from C-terminus to N-terminus in step 1) is Fmoc-Cys(Me)-OH, Fmoc-Gly-OH, Fmoc-Thr(tBu)-OH, Fmoc-Cys(Dpm)-OH, Fmoc-Ala-OH, Fmoc-Pro-OH, Fmoc-Asn(Trt)-OH, Fmoc-Cys(Mmt)-OH, Fmoc-Cys(Me)-OH, Fmoc-Tyr(tBu)-OH, Fmoc-Glu(tBu)-OH, Fmoc-Cys(Dpm)-OH and Fmoc-Cys(Mmt)-OH. The process for obtaining the linaclotide precursor resin comprises:

a) reacting Fmoc-Tyr(tBu)-OH with a carrier resin to obtain Fmoc-Tyr(tBu)-resin;

b) removing Fmoc followed by washing the resin with a solvent until the complete removal of Fmoc is detected by a detection method;

c) dissolving and activating an appropriate amount of amino acid to be coupled and a coupling agent in a solvent, and then adding them together into a solid phase reaction column until the termination of the reaction is detected by a detection method; and d) repeating b) and c).

Wherein, the detection method applied is any one known in the art to achieve this purpose, such as chromatography or chemical calibration, preferably using an reagent, the reaction endpoint of which can be determined, preferably ninhydrin. When ninhydrin is used, the development of the resin indicates that there is a free amine in the polypeptide, i.e., there is no protecting group on the amine.

Wherein, reagent for removing Fmoc is 20% piperidine/DMF solution (DBLK), that is, a mixed solution of piperidine and DMF with a volume ratio of 1:4

Wherein, the coupling agent is a composition of (N,N'-diisopropylcarbodiimide) DIC and Compound A, or a composition of DIPEA and Compound A and Compound B, preferably a composition of DIC and Compound A, wherein Compound A is HOBt or HOAt and Compound B is PyBOP, PyAOP, HATU, HBTU or TBTU; the components in the coupling agent is in a molar ratio of DIC:A=1.2:1.1 and DIPEA:A:B=2.0:1.1:1.0.

Wherein, the reaction of step c) is performed in a solid phase reaction column. The solid phase reaction column is not particularly limited and may be any solid phase reaction column that can achieve this purpose. In addition, the coupling reaction for each amino acid is performed for usually 1.5-4 hours, preferably 2-3 hours; the pressure is preferably normal pressure, and it can also be performed under a properly increased or decreased pressure; the temperature is preferably room temperature (i.e., 20±5° C.), and it can also be carried out at a properly elevated or reduced temperature.

Wherein, the resin is swelled before each coupling step, wherein the reagent used can be any reagent in the art that can achieve this purpose, such as DMF, (N-methylpyrrolidone) NMP, and dichloromethane, preferably DMF.

Wherein, the solvent used in the washing step can be any reagent in the art that can achieve this purpose, such as DMF, NMP, and dichloromethane, preferably DMF.

In the method for preparing linaclotide of the present invention, the deprotecting agent in step 2) is a mixed solution of TFA/DCM, and the volume concentration of TFA in the mixed solution is 1%-10%, preferably 1%-5%, and the reaction endpoint is a change in the solution from red to colourless.

In the method for preparing linaclotide of the present invention, the oxidizing agent in step 3) is selected from $H_2O_2$ and NCS, preferably NCS, and the solvent used is selected from the group consisting of DMF, NMP and dichloromethane, preferably DMF.

In the method for preparing linaclotide of the present invention, wherein the lysing solution in step 4) is a mixture of TFA, $H_2O$, PhOMe and thioanisole in a different ratio, preferably a mixture of TFA, $H_2O$, PhOMe and thioanisole in a volume ratio of 90:5:4:1.

In the method for preparing linaclotide of the present invention, the oxidizing agent in step 5) is selected from H2O2 and NCS, and the molar ratio between the oxidizing agent and the mono-dithio cyclic peptide obtained in step 4) is 1:10-10:1; preferably, the oxidizing agent is NCS and the molar ratio between NCS and the mono-dithio cyclic peptide obtained in step 4) is 1:1-10:1, preferably 2:1; and the solvent is selected from the group consisting of methanol, ethanol, acetone, tetrahydrofuran, acetonitrile, and a mixed solution of the above solvent and water in a different ratio, preferably a mixed solution of acetonitrile and water, wherein the volume ratio between acetonitrile and water is 1:1-1:5, preferably 1:1.

In the method for preparing linaclotide of the present invention, the reagent used in step 6) to enable demethylation and oxidation synchronously is selected from the group consisting of horseradish peroxidase, mushroom tyrosinase, and monoamine oxidase. The mass ratio between the reagent to enable demethylation and oxidation synchronously and the bis-dithio cyclic peptide obtained in step 5) is 0.5:1000-10:100. Preferably, the reagent is horseradish peroxidase, and the mass ratio between horseradish peroxidase used and the bis-dithio cyclic peptide obtained in step 5) is 0.5:100-10:100, more preferably 1.5:100-2.5:100, and most preferably 2.0:100.

In the method for preparing linaclotide of the present invention, purification is carried out by reverse phase high pressure liquid chromatography. Both the bis-dithio cyclic peptide and the final product—linaclotide, can be purified by reverse phase high pressure liquid chromatography. Furthermore, in the reverse phase high pressure liquid chromatography, reverse phase octadecylsilane is used as a stationary phase, 0.1 vol % aqueous acetic acid/acetonitrile is used as a mobile phase, wherein a volume ratio between 0.1 vol % aqueous acetic acid and acetonitrile in the mobile phase is preferably 98:2 to 50:50, more preferably 80:20 to 60:40, and most preferably 70:30. Target peak fractions are collected, concentrated and lyophilized.

In the present invention, although the oxidizing agent used to form the first and second disulfide bonds may be the same (e.g., NCS), a strategy is used so as to achieve selective formation of the first and second disulfide bonds wherein the protecting groups Mmt in the linaclotide precursor resin is firstly removed in a mixed solution of TFA/DCM, and then the first disulfide bond is formed by solid phase oxidation, followed by removing the protecting groups Dpm while cleaving the resin the linaclotide precursor resin containing a mono-dithio ring by a lysing solution, and then forming the second disulfide bond by liquid phase oxidation, since the protecting groups Mmt of Cys at positions 1 and 6 are removed in dilute TFA solution, while the protecting groups Dpm of Cys at positions 2 and 10 must be removed in concentrated TFA.

In the present invention, Fmoc-Cys(Me)-OH is used as a raw material, which is advantageous to oxidative coupling of the third disulfide bond and removal of the protecting group methyl of cysteine at the same time to obtain linaclotide. Horseradish peroxidase is preferably used in this step, which is used as both a demethylating agent and an oxidizing agent, so that demethylation and oxidation can be achieved simultaneously.

In summary, as compared to the prior art, the present invention employs a method for synthesizing linaclotide by completely selectively forming three disulfide bonds, wherein a linaclotide precursor resin is firstly prepared by solid phase synthesis, and then the first disulfide bond is formed by solid phase oxidation; a cleavage reaction is conducted and then the second disulfide bond is formed by liquid phase oxidation again; finally, the methyl group of the methyl protected cysteine is removed, and at the same time the third disulfide bond is oxidatively coupled to obtain linaclotide.

The method of the present invention avoids the production of disulfide bond mismatched isomers by completely selectively forming three disulfide bonds to obtain a higher purity and yield. Meanwhile, the first disulfide bond is formed by solid phase oxidation before the cleavage reaction of the linaclotide precursor resin, so as to reduce the difficulty in the formation of the first disulfide bond. Moreover, the raw material used in the preparation of the third disulfide bond is cheaper methyl protected cysteine, and the removal of the protecting group methyl and oxidative coupling of cysteine are achieved synchronously.

The synthetic method has the advantages of high product purity, high yield, simple and easily available raw materials, low cost, simple and stable processes, and being suitable for large-scale production, and the like, and furthermore exhibits a widespread application prospect in the technical field of polypeptide drug synthesis.

BRIEF DESCRIPTION OF THE DRAWINGS

FIG. 1 is a schematic diagram of a synthetic route of the present invention.

DETAILED DESCRIPTION OF EMBODIMENTS

Hereinafter, the present invention will be further described in detail by way of examples, which are intended to illustrate the present invention rather than limit the present invention. It should be noted that, for those skilled in the art, several improvements and modifications can be made to the present invention without departing from the principle of the present invention, and these improvements and modifications also fall within the protection scope of the present invention.

The meanings of the abbreviations used in the present invention are listed in the table below.

| Abbreviations | Meanings |
|---|---|
| HOAt | 1-hydroxy-7-azobenzotriazole |
| Fmoc | 9-fluorenylmethoxycarbonyl |
| HOBt | 1-hydroxybenzotriazole |
| HATU | 2-(7-azobenzotriazole)-N,N,N',N'-tetramethyluronium hexafluorophosphate |
| HBTU | Benzotriazole-N,N,N',N'-tetramethyluronium hexafluorophosphate |
| DIPEA | N,N-diisopropylethylamine |
| PyBOP | Benzotriazol-1-yl-oxytripyrrolidinyl hexafluorophosphate |
| PyAOP | (3H-1,2,3-triazolo[4,5-b]pyridin-3-yloxy)tri-1-pyrrolidinylphosphonium hexafluorophosphate |
| TBTU | O-benzotriazole-N,N,N',N'-tetramethyluronium tetrafluoroborate |
| DMF | N,N-dimethylformamide |
| DCM | Dichloromethane |
| NCS | N-chlorosuccinimide |
| TFA | Trifluoroacetic acid |
| PhOMe | Anisole |
| EDT | Ethanedithiol |
| DBLK | 20% piperidine/DMF (V/V) solution |
| tBu | Tert-butyl |
| Trt | Triphenylmethyl |
| Acm | Acetamide methyl |
| Mmt | 4-methoxytrityl |
| Fmoc | 9-fluorenylmethoxycarbonyl |
| Dpm | Diphenylmethyl |
| DIC | Diisopropylcarbodiimide |
| NMP | N-methylpyrrolidone |
| DMAP | 4-dimethylaminopyridine |
| DIPCDI | Diisopropylcarbodiimide |
| EDC•HCl | 1-ethyl-(3-dimethylaminopropyl)-carbodiimide hydrochloride |
| THF | Tetrahydrofuran |
| TA | Thioanisole |
| pMeOBzl | p-methoxybenzyl |
| EDT | Ethanedithiol |
| Acm | Acetamide methyl |

The raw materials and reagents used in the method for preparing linaclotide are all commercially available and purchased from GL Biochem (Shanghai) Ltd., Chengdu Zhengyuan Biochemical Technology Co., Ltd. and Suzhou Tianma Specialty Chemicals Co., Ltd., respectively.

Example 1: Preparation of Fmoc-Tyr(tBu)-Wang Resin with a Degree of Substitution of 0.50 mmol 100 g of Wang resin with a degree of substitution of 1.0 mmol/g was weighed and put into a solid phase reaction column, 150 ml of DMF was added, and the mixture was sparged and swelled with nitrogen for 60 min. Fmoc-Tyr(tBu)-OH (45.9 g, 100 mmol), HOBt (16.2 g, 120 mmol) and DMAP (1.2 g, 10 mmol) were weighed and dissolved in 100 ml of DMF, DIC (20.3 ml, 117.1 mmol) was added at 0° C., and the mixture was activated for 5 min and added into the reaction column. After two hours of reaction, acetic anhydride (70 ml) and pyridine (60 ml) were added, mixed and blocked for 24 hours and washed 3 times with DCM (100 ml/time). The resin was shrunk with methanol and suctioned dry to give 150 g of Fmoc-Tyr(tBu)-Wang resin. The degree of substitution was detected to be 0.50 mmol/g.

Example 2: Preparation of Linaclotide Precursor Resin 50 g Fmoc-Tyr(tBu)-Wang resin (25 mmol) with a degree of substitution of 0.50 mmol/g prepared in Example 1 was weighted and put into a solid-phase reaction column, 50 ml of DMF was added, and the mixture was sparged and swelled with nitrogen for 60 min, and then deprotected twice with DBLK2 (50 ml/time) for 6 min and 8 min respectively, and washed with DMF 6 times (100 ml/time). Fmoc-Cys (Me)-OH (48.7 g, 75 mmol) and HOBt (11.7 g, 75 mmol) were weighted and dissolved in 100 ml DMF, and DIC (13 ml, 75 mmol) was added in an ice water bath to be activated for 3 min. Then, the mixture was added into a reaction column and reacted at room temperature for 2 h, and the end point of the reaction was detected with ninhydrin (the reaction was terminated if the resin was colorless and transparent; the reaction was prolonged for 1 h if the resin was developed). After the reaction was completed, the resin was washed three times with DMF (100 ml/time), DBLK was added for deprotection twice (100 ml/time) for 6 min and 8 min, respectively. The resin was washed with DMF six times (100 ml/time) and showed color with ninhydrin detection.

The above coupling procedure was repeated, and Fmoc-Gly-OH, Fmoc-Thr(tBu)-OH, Fmoc-Cys(Dpm)-OH, Fmoc-Ala-OH, Fmoc-Pro-OH, Fmoc-Asn(Trt)-OH, Fmoc-Cys(Mmt)-OH, Fmoc-Cys(Me)-OH, Fmoc-Tyr(tBu)-OH, Fmoc-Glu(tBu)-OH, Fmoc-Cys(Dpm)-OH, and Fmoc-Cys(Mmt)-OH were coupled in sequence to the peptide in the order from C-terminus to N-terminus. In each coupling step, 50 g resin with a degree of substitution of 0.50 mmol/g obtained in the previous step, 75 mmol each of the above-mentioned amino acids, HOBt, and DIC were added. After all the above coupling procedures were completed, the resin was shrunk with methanol and suctioned dry to obtain 107.6 g of linaclotide precursor resin.

Example 3: Removal of Protecting Group Mmt 107.6 g of the linaclotide precursor resin obtained in Example 2 was swelled in 1 liter of DMF solution for 1 h, the solution was then suctioned away under reduced pressure, and the resin was washed twice with DCM (500 ml/time). The resin was washed with 250 ml of 2% TFA/DCM (v/v) solution for 2 min each time until the color of the resin changed from red to colorless, then washed twice with DCM (500 ml/time) and washed twice with DMF (500 ml/time). Then, the solution was suctioned away under reduced pressure.

Example 4: Preparation of Linaclotide Precursor Resin Containing a Mono-Dithio Ring 1 liter of DMF was added to the resin without protecting group Mmt obtained in Example 3, and then NCS (5.34 g, 40 mmol) was added. After half an hour of reaction, the solution was suctioned away under reduced pressure and the resin was washed three times with DMF (500 ml/time). 500 ml of methanol was added to shrink the resin for 30 min, then methanol was suctioned away, and vacuum drying was performed to obtain 92.2 g of resin.

Example 5: Preparation of Mono-Dithio Cyclic Peptide 92.2 g of the resin obtained in Example 4 was added to a 1 L three-necked bottle, 900 ml of a preformulated solution TFA:$H_2O$:PhOMe:thioanisole=90:5:4:1 (V:V) was added and reacted at room temperature for 2 h. The resin was filtered under reduced pressure and the filtrate was collected. The resin was washed with a small amount of TFA and the filtrates were combined. The filtrate was slowly added to 10 L of cold diethyl ether, precipitated, centrifuged, washed with cold diethyl ether 5 times (5 L/time), and dried under reduced pressure to obtain 25.3 g of crude peptides with HPLC purity of 70.6%.

Example 6: Preparation of Bis-Dithio Cyclic Peptides 16.1 g of mono-dithio cyclic peptides obtained in Example 5 were dissolved in 500 ml of 50% acetonitrile/water (v/v) solution, NCS (2.67 mg, 0.02 mmol) was added, and reacted at room temperature for 2 h. After the oxidation is completed, the mixture was directly loaded onto a 10 cm×25 cm preparative column for purification and preparation. The purification conditions were that: reverse phase octadecylsilane was used as a stationary phase; the mobile phase A was 0.1% acetic acid/water (v/v) solution and phase B was acetonitrile with A:B=70:30 (in volume) for isocratic elution; the flow rate was 70-80 ml/min; and the detection wavelength was 230 nm. Target peak fractions were collected, concentrated and lyophilized to give 14.5 g pure products with purity of 96% and yield of 90%.

Example 7: Preparation of Linaclotide 14.5 g of bis-dithio cyclic peptides obtained in Example 6 were dissolved in 300 ml of acetonitrile, 280 ml of sodium dihydrogen phosphate buffer solution (pH=6) was added, and then 300 mg of horseradish peroxidase was added. After 1 hour of reaction, the mixture was directly loaded onto a 10 cm×25 cm preparative column for purification and preparation. Reverse phase octadecylsilane was used as a stationary phase; the mobile phase A was 0.1% acetic acid/water (v/v) solution and phase B was acetonitrile with A:B=70:30 (in volume) for isocratic elution; the flow rate was 70-80 ml/min; and the detection wavelength was 280 nm. Target peak fractions were collected, concentrated and lyophilized to give 10.0 g pure product with purity of 99.5% and yield of 70%.

The invention claimed is:
1. A synthesis method of linaclotide, comprising the following steps:
 1) preparing a linaclotide precursor resin by reacting Fmoc-Tyr(tBu)-OH with a carrier resin to obtain Fmoc-Tyr(tBu)-resin, and coupling Fmoc-AA-OH one by one in the order from C-terminus to N-terminus with the Fmoc-Tyr(tBu)-resin as a solid phase carrier to obtain the linaclotide precursor resin, wherein the side chains of Cys corresponding to positions 5 and 13 of linaclotide are protected by Me, the side chains of Cys corresponding to positions 1 and 6 of linaclotide are protected by Mmt, and the side chains of Cys corresponding to positions 2 and 10 of linaclotide are protected by Dpm;
 2) removing the Mmt protecting groups from the linaclotide precursor resin obtained in step 1) with a deprotecting agent;
 3) oxidizing the linaclotide precursor resin obtained in step 2) with an oxidizing agent to form a first disulfide bond to obtain a linaclotide precursor resin containing a mono-dithio ring;
 4) cleaving the resin in the linaclotide precursor resin containing a mono-dithio ring obtained in step 3) and simultaneously removing the Dpm protecting groups with a lysing solution to obtain a mono-dithio cyclic peptide;
 5) oxidizing the mono-dithio cyclic peptide obtained in step 4) with an oxidizing agent to form a second disulfide bond to obtain a bis-dithio cyclic peptide; and
 6) removing the methyl protecting groups of Cys from the bis-dithio cyclic peptide obtained in step 5) and simultaneously oxidizing to form a third disulfide bond with a demethylating and oxidizing agent to obtain linaclotide.

2. The synthesis method of linaclotide according to claim 1, wherein the coupling of Fmoc-AA-OH in the order from C-terminus to N-terminus in step 1) is Fmoc-Cys(Me)-OH, Fmoc-Gly-OH, Fmoc-Thr(tBu)-OH, Fmoc-Cys(Dpm)-OH, Fmoc-Ala-OH, Fmoc-Pro-OH, Fmoc-Asn(Trt)-OH, Fmoc-Cys(Mmt)-OH, Fmoc-Cys(Me)-OH, Fmoc-Tyr(tBu)-OH, Fmoc-Glu(tBu)-OH, Fmoc-Cys(Dpm)-OH and Fmoc-Cys(Mmt)-OH.

3. The synthesis method according to claim 1, wherein the preparation of the linaclotide precursor resin in step 1) comprises: a) reacting Fmoc-Tyr(tBu)-OH with a carrier resin to obtain Fmoc-Tyr(tBu)-resin; b) removing Fmoc followed by washing the resin with a solvent until the complete removal of Fmoc is detected by a detection method; c) dissolving and activating an appropriate amount of amino acid to be coupled and a coupling agent in a solvent, and then adding them together into a solid phase reaction column until the termination of the reaction is detected by a detection method; and d) repeating b) and c);
 wherein reagent for removing Fmoc is 20% piperidine/DMF solution (DBLK), that is, a mixed solution of piperidine and DMF with a volume ratio of 1:4;
 wherein the coupling agent is a composition of (N,N'-diisopropylcarbodiimide) DIC and Compound A, or a composition of DIPEA and Compound A and Compound B, preferably a composition of DIC and Compound A, wherein Compound A is HOBt or HOAt and Compound B is PyBOP, PyAOP, HATU, HBTU or TBTU; the components in the coupling agent is in a molar ratio of DIC:A equal 1.2:1.1 and DIPEA:A:B equal 2.0:1.1:1.0; and
 wherein the resin is swelled before coupling, and the solvent is selected from the group consisting of DMF, (N-methylpyrrolidone) NMP, and dichloromethane.

4. The synthesis method according to claim 1, wherein the carrier resin in step 1) is wang resin or 2-chloro resin, with a degree of substitution of 0.1-1.0 mmol/g, preferably 0.2-0.8 mmol/g, and more preferably 0.2-0.5 mmol/g.

5. The synthesis method according to claim 1, wherein the deprotecting agent in step 2) is a mixed solution of TFA/DCM, and the volume concentration of TFA in the mixed solution is 1%-40%, preferably 1%-5%.

6. The synthesis method according to claim 1, wherein the oxidizing agent in step 3) is selected from $H_2O_2$ and NCS, and the solvent is selected from the group consisting of DMF, NMP and dichloromethane.

7. The synthesis method according to claim 1, wherein the lysing solution in step 4) is a mixture of TFA, $H_2O$, PhOMe and thioanisole in a volume ratio of TFA:H2O:PhOMe:thioanisole equal 90:5:4:1.

8. The synthesis method according to claim 1, wherein the oxidizing agent in step 5) is selected from $H_2O_2$ and NCS, and the molar ratio between the oxidizing agent and the mono-dithio cyclic peptide obtained in step 4) is 1:10-10:1; and the solvent is selected from the group consisting of methanol, ethanol, acetone, tetrahydrofuran, acetonitrile, and a mixed solution of the above solvent and water in a different ratio.

9. The synthesis method according to claim 1, wherein in step 6), the demethylating and oxidizing agent is selected from the group consisting of horseradish peroxidase, mushroom tyrosinase, and monoamine oxidase, and the mass ratio between the demethylating and oxidizing agent and the bis-dithio cyclic peptide obtained in step 5) is 0.5:1000-10:100.

10. The synthesis method according to claim 1, further comprising a step of: 7) purifying linaclotide by reverse phase high pressure liquid chromatography.

11. The synthesis method according to claim 8, wherein the oxidizing agent is NCS and the molar ratio between NCS and the mono-dithio cyclic peptide obtained in step 4) is 1:1-10:1; and the solvent is a mixed solution of acetonitrile and water, wherein the volume ratio between acetonitrile and water is 1:1-1:5.

12. The synthesis method according to claim 11, wherein the molar ratio between NCS and the mono-dithio cyclic peptide obtained in step 4) is 2:1; and wherein the volume ratio between acetonitrile and water is 1:1.

13. The synthesis method according to claim 9, wherein the demethylating and oxidizing agent is horseradish peroxidase, and the mass ratio between horseradish peroxidase and the bis-dithio cyclic peptide obtained in step 5) is 0.5:100-10:100.

14. The synthesis method according to claim 13, wherein the mass ratio between horseradish peroxidase and the bis-dithio cyclic peptide obtained in step 5) is 1.5:100-2.5:100.

15. The synthesis method according to claim 13, wherein the mass ratio between horseradish peroxidase and the bis-dithio cyclic peptide obtained in step 5) is 2.0:100.

* * * * *